United States Patent [19]

Harandi et al.

[11] Patent Number: 5,030,782

[45] Date of Patent: * Jul. 9, 1991

[54] LIGHT ALKANE CONVERSION

[75] Inventors: Mohsen N. Harandi, Lawrenceville; Hartley Owen, Belle Mead, both of N.J.

[73] Assignee: Mobil Oil Corporation, Fairfax, Va.

[*] Notice: The portion of the term of this patent subsequent to Mar. 27, 2007 has been disclaimed.

[21] Appl. No.: 347,297

[22] Filed: May 4, 1989

[51] Int. Cl.$^5$ .................... C07C 12/02; C07C 5/333
[52] U.S. Cl. .................... 585/322; 585/415; 585/660
[58] Field of Search .......... 585/322, 319, 407; 208/159, 172

[56] References Cited

U.S. PATENT DOCUMENTS

| | | | |
|---|---|---|---|
| 2,769,693 | 11/1956 | Bearer | 208/172 |
| 3,756,942 | 9/1973 | Cattanach | 208/137 |
| 3,759,821 | 9/1973 | Brennan et al. | 208/93 |
| 3,760,024 | 9/1973 | Cattanach | 260/673 |
| 4,784,748 | 11/1988 | Avidan et al. | 208/159 |
| 4,912,273 | 3/1990 | Harandi et al. | 585/322 |

OTHER PUBLICATIONS

N. Y. Chen et al., "M2 Forming-A Process for Aromatization of Light Hydrocarbons", Ind. Eng. Chem. Process D&s. Dev. 25, pp. 151-155 (1986).

Kirk-Othmer Encyclopedia of Chemical Technology, 3rd. ed., vol. 9, pp. 706-709 (1980).

*Primary Examiner*—Asok Pal
*Attorney, Agent, or Firm*—Alexander J. McKillop; Charles J. Speciale; Robert B. Furr, Jr.

[57] ABSTRACT

Aliphatics are aromatized in a two-stage catalytic upgrading process. In the first stage, aliphatic hydrocarbons are at least partially cracked and dehydrogenated to form an intermediate product stream. The extent and selectivity of the cracking and dehydrogenation reactions are preferably controlled to maintain heat balance in a second stage catalytic aromatization step.

In a preferred embodiment, a first aliphatic feedstream is cracked and dehydrogenated to form an intermediate product stream. The intermediate product stream is then mixed with a second aliphatic feedstream and contacted with a zeolite aromatization catalyst. Cracking and dehydrogenation of the first aliphatic feedstream is controlled to provide heat balanced aromatization of the combined streams.

24 Claims, 1 Drawing Sheet

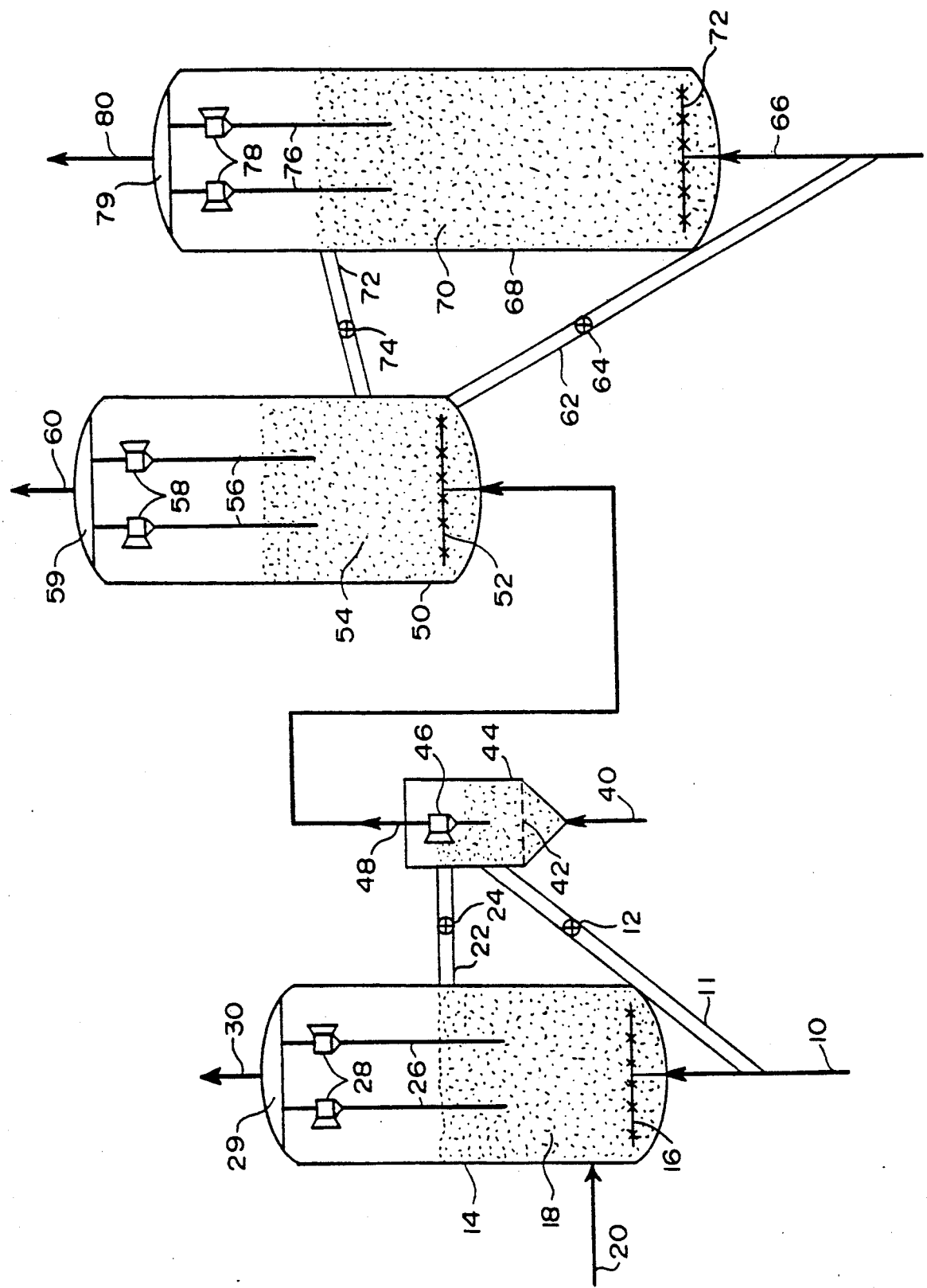

LIGHT ALKANE CONVERSION

FIELD OF THE INVENTION

This invention relates to the field of hydrocarbon upgrading processes. In particular, the invention relates to an improved method and apparatus for aromatizing an aliphatic feedstream.

BACKGROUND OF THE INVENTION

Both dehydrogenation and aromatization of paraffinic feeds are highly endothermic reactions. Aromatization is believed to proceed via a two-step mechanism which first includes dehydrogenation and cracking of paraffins to form an olefinic intermediate and then dehydrocyclization of the olefinic intermediate to form aromatics. This mechanism was recognized by the teachings of U.S. Pat. No. 3,845,150 to Yan and Zahner which disclosed co-feeding a light olefinic supplemental feed stream together with a paraffinic stream to balance heat input to a catalytic aromatization zone. A second paraffinic stream may be dehydrogenated if a suitable light olefinic stream is not available.

Previous processes employing a single catalyst to promote paraffin aromatization have necessarily operated at less than optimal efficiency due predominately to two factors. First, relatively heavy coke deposition on the aromatization catalyst necessitated frequent regeneration and a relatively high rate of fresh catalyst make up. Second, previous processes were limited by inefficient heat transfer to the reaction zone.

Typical paraffin aromatization unit feedstreams readily form coke when raised to temperatures above about 450° C. (1000° F.) Coke precursors in the feed including oxygenates such as glycol readily react to form coke upon contact with the hot catalyst. This coke accumulates on the catalyst and blocks access to the active sites. Thus, both the catalytic activity as well as the aromatics selectivity are diminished as coke builds up on the catalyst.

Moreover, the relatively heavy coke loading on the catalyst increases heat input to the regenerator. This incremental heat input is disadvantageous as this additional heat must be removed to maintain the regenerator operating temperature. Excessively high regenerator temperatures can result in catalyst deactivation. The elevated regeneration temperatures usually associated with highly coked catalyst tend to accelerate steam deactivation. Steam deactivation, an irreversible physical degradation of the catalyst, is an integral function of time, temperature and water partial pressure. Therefore, the deposition of additional coke on the aromatization catalyst is clearly undesirable.

Previous processes for the fluid-bed aromatization of paraffins were still further limited by relatively inefficient heat transfer. Fresh feed was typically preheated in a process furnace to as high a temperature as could be sustained without excessive coke formation on the inside walls of the furnace tubes or other downstream facilities. Next, the fresh preheated feed was charged to the fluid-bed aromatization reactor where the hot fluidized catalyst brought the feedstream to reaction temperature almost immediately. Characteristics of the catalyst and the feed require that in this process configuration the bulk of the heat transferred to the feedstock be transferred by relatively inefficient indirect transfer. A more efficient method to heat the feed to reaction temperature would be by direct exchange with hot catalyst particles. At catalyst to feedstock ratios suitable for aromatization, however, the ratio of catalyst mass to feedstock mass and the heat input required by the strongly endothermic reaction would necessitate extreme catalyst temperatures. Raising the catalyst to such temperatures would likely cause a precipitous and permanent loss of activity.

From the foregoing, it can well be seen that direct heat transfer would be preferable over indirect due to its higher efficiency, particularly in a strongly endothermic fluid-bed reaction carried out at high temperature. Further, it is also clear that increasing the efficiency of the indirect heat transfer by raising the process furnace tube wall temperature would afford the desired increase in efficiency for only a brief period of time until the feedstock began insulating itself from the tube walls with a layer of coke, or until the accumulation of coke resulted in other even more detrimental operational problems. The most desirable heat transfer configuration would provide the efficiency of direct exchange while avoiding damage to the catalyst. Thus it would be highly beneficial to combine the advantages of direct heat transfer with those of a heat balanced reaction zone.

SUMMARY OF THE INVENTION

The present invention provides an improved method and apparatus for the conversion of an aliphatic feedstream to an aromatic product stream. As discussed above, the aromatization reaction is believed to proceed by a two-step mechanism. The present invention partially segregates these steps into two separate fluid-bed reaction zones. By completely separating these two reaction zones, each zone may be operated under optimum conditions to maximize heat transfer efficiency as well as aromatics selectivity and yield while prolonging the life of the costly aromatization catalyst.

The first reaction zone converts a paraffinic feed stream to a reactor effluent stream containing olefins. This first reaction zone may be operated in a dehydrogenation mode, a cracking mode, or a cracking/dehydrogenation intermediate mode, with the intermediate mode being the most preferred. For the purpose of this disclosure, this first reaction zone is called the dehydrogenation zone. Easily fluidized finely divided particles are heated by direct exchange in a fluid-bed combustion zone. The inert particles are then withdrawn from the combustion zone and charged to a dehydrogenation zone together with fresh aliphatic feedstock where at least a portion of the paraffins in the aliphatic feedstock are either dehydrogenated, cracked or partially dehydrogenated and partially cracked.

The invention overcomes the shortcomings of previous aromatization methods by tailoring the process configuration to the mechanism of the reaction as understood. By segregating the reaction into a dehydrogenation stage and a dehydrocyclization stage, the invention provides optimum conversion conditions in each zone as mentioned above. For example, the first step of a paraffin aromatization reaction is understood to be a highly endothermic paraffin dehydrogenation/cracking reaction which is typically carried out above about 540° C. (1000° F.) and preferably above 620° C. (1150° F.). Dehydrogenation zone effluent, called intermediate product, is typically rich in olefins and preferably contains a substantial amount of ethylene. Advantageously, the stream flows out of the dehydrogenation zone preheated to near aromatization reaction temperature. The intermediate product stream is then charged to the fluid-bed catalytic aromatization zone where the intermediate product undergoes dehydrocyclization to form an aromatic product stream.

The intermediate product temperature highlights yet another benefit of the invention, namely that by maintaining the reaction system in two separate reaction zones, the feed is preheated by direct exchange. Indirect heat transfer, exemplified by passing a first fluid through heat exchange coils immersed in a second fluid, is inherently less efficient than direct heat transfer, exemplified by mixing a hot fluid with a cold fluid. The commercialization of high temperature strongly endothermic processes such as paraffin aromatization may stand or fall based on the feasibility of transferring sufficient heat to the fluid-bed reaction zone at the required elevated temperatures. The invention thus further advances the commercial potential of fluid-bed aromatization by replacing inefficient indirect heat transfer with highly efficient direct heat transfer.

The first reaction stage, including dehydrogenation and cracking, is endothermic. Depending on the degree of conversion in the first stage, the second stage may range from mildly endothermic to mildly exothermic. For example, relatively complete conversion of paraffins to olefins in the first reaction stage will yield exothermic dehydrocyclization in the second reaction stage.

The present invention therefore provides a process for the conversion of an aliphatic feedstream to an aromatic product stream comprising the steps of combusting fuel to heat a fluid bed of finely divided solid particles maintained within a combustion zone, withdrawing a stream of hot finely divided solid particles from the combustion zone, contacting the stream of hot finely divided solid particles with the aliphatic feedstream in a fluid-bed dehydrogenation zone under dehydrogenation conversion conditions for a period of time sufficient to preheat the aliphatic feedstream and to partially crack and partially dehydrogenate the aliphatic feedstream to form an intermediate product stream, and contacting the intermediate product stream with an aromatization catalyst in a fluid-bed aromatization zone under aromatization conversion conditions.

In its apparatus aspects, the invention comprises a combustion vessel for burning fuel in contact with a fluid bed of finely divided solid particles, a dehydrogenator vessel in valved communication with the combustion vessel for contacting hot finely divided solid particles withdrawn from the combustion vessel with an aliphatic feedstream to form an intermediate product stream, and an aromatization reactor in communication with the dehydrogenator vessel for aromatizing the intermediate product stream. The apparatus of the invention may further comprise a continuous regenerator for regenerating the aromatization catalyst.

BRIEF DESCRIPTION OF THE DRAWING

The FIGURE is a simplified schematic diagram of the process of the present invention.

DETAILED DESCRIPTION

The invention provides a process and apparatus for improving yield and selectivity in a paraffin aromatization process while significantly reducing energy and catalyst makeup expenses. By dividing the fluid-bed process into two separate and distinct reaction zones, the conditions in each zone are tailored to fit the conversion process proceeding in that particular zone.

Paraffin dehydrogenation or cracking is understood to be the first step in paraffin aromatization. In the first reaction zone, the fresh paraffinic feed contacts a fluid bed of hot finely divided solids to preheat and at least partially dehydrogenate and/or crack the feed. The main dehydrogenation reaction proceeds more quickly if the finely divided solids include a dehydrogenation catalyst as described below. However, thermal dehydrogenation or cracking proceeds at a rate sufficient for the purposes of the invention in the presence of inert solids. Thus, it is preferable but not critical for the finely divided solids in the dehydrogenation zone to comprise dehydrogenation catalyst, and the process functions satisfactorily with catalytically inert solids circulating through the dehydrogenation zone.

The dehydrogenation zone may either dehydrogenate, crack, or both dehydrogenate and crack its paraffinic feedstock. The particular reactions favored will be a function of process conditions and will further be controlled by the composition of the finely divided solids circulating through the dehydrogenation zone.

Olefins generally aromatize exothermically. Ethylene aromatization generates more heat per unit mass than aromatization of heavier olefins. Thus to maximize heat input to the downstream aromatization reactor, the dehydrogenation zone is operated in a cracking mode.

The finely divided solids in the dehydrogenation reaction zone are withdrawn and charged to a combustion chamber where they are reheated by the combustion of fuel in a fluid bed to temperatures typically exceeding 870° C. (1600° F.). The most preferred fuels are hydrogen-deficient fuels, examples of which include charcoal and coke. Hydrogen-deficient fuels are preferred to minimize the evolution of water during the combustion reaction which is carried downstream and eventually contacts the aromatization catalyst. The preferred aromatization catalysts, medium-pore zeolites, undergo an irreversible physical degradation when exposed to water at elevated temperatures.

At this point in the description of the invention, several advantages are already apparent. The fresh paraffinic feed has been preheated and at least partially dehydrogenated. A substantial portion of the coke precursors in the fresh feed have reacted to form coke which was deposited on the fluidized solids in the dehydrogenation zone. Thus, the paraffinic feed has been prepared for catalytic aromatization by increasing its olefin content, decreasing its propensity to coke the aromatization catalyst and by preheating the partially dehydrogenated feed to aromatization reaction temperature. This conversion to the intermediate product stream has been carried out using energy-efficient direct heat transfer via fluidized solid particles.

The intermediate product stream is now charged to the aromatization reactor. Because olefin aromatization is strongly exothermic, the composition of the intermediate product stream is preferably adjusted to provide heat balanced operation in the aromatization reactor. Intermediate product stream composition may be adjusted by varying the reaction severity in the dehydrogenation zone, with and lower feedstock space velocities yielding more olefinic intermediate product stream compositions.

In the fluid-bed reaction zone of the aromatization reactor, the intermediate product stream is readily upgraded to aromatic product. The aromatization catalyst deactivates much more slowly and requires less makeup catalyst addition than in single reaction zone systems due in particular to two factors. First, reacting at least a portion of coke precursors upstream from the aromatization reactor decreases coke deposition on the aromatization catalyst. Second, decreased coking of the aromatization catalyst enables the aromatization catalyst regenerator to oxidatively regenerate the catalyst at lower temperatures, thereby decreasing the rate of steam deactivation. Both factors act in concert to improve the selectivity of the catalyst for the formation of valuable aromatic products including benzene, toluene and xylene.

Aromatization Process

Hydrocarbon upgrading reactions compatible with the process of the present invention include both the conversion of aliphatic hydrocarbons to aromatic hydrocarbons. Such conversions are discussed by N. Y. Chen and T. Y. Yan in their article "M2 Forming-A Process for Aromatization of Light Hydrocarbons", 25 IND. ENG. CHEM. PROCESS DES. DEV. 151 (1986), the text of which is incorporated herein by reference. The following representative U.S. patents detail the feed compositions and process conditions for the aromatization and dehydrogenation reactions. Aromatization and dehydrogenation process conditions are summarized in Table 1.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2$-$C_4$ paraffins and/or olefins with a crystalline aluminosilicate, e.g. ZSM-5.

Hydrocarbon feedstocks which can be converted according to the present process include various refinery streams including coker gasoline, light FCC gasoline, $C_5$-$C_7$ fractions of straight run naphthas and pyrolysis gasoline, as well as raffinates from a hydrocarbon mixture which has had aromatics removed by a solvent extraction treatment. Examples of such solvent extraction treatments are described on pages 706-709 of the *Kirk-Othmer Encyclopedia of Chemical Technology*, Third Edition, Vol. 9 (1980). A particular hydrocarbon feedstock derived from such a solvent extraction treatment is a Udex raffinate. The paraffinic hydrocarbon feedstock suitable for use in the present process may comprise at least 75 percent by weight, e.g. at least 85 percent by weight, of paraffins having from 5 to 10 carbon atoms.

TABLE 1

| WHSV | Broad range: 0.3-500 hr$^{-1}$ |
| --- | --- |
| | Preferred range: 1-50 hr$^{-1}$ |
| OPERATING PRESSURE | Broad: 170-2170 kPa (10-300 psig) |
| | Preferred: 310-790 kPa (30-100 psig) |
| OPERATING | Broad: 500-820° C. (930-1500° F.) |

TABLE 1-continued

| TEMPERATURE | Preferred: 560-620° C. (1050-1150° F.) |
| --- | --- |

Aromatization Catalysts

The members of the class of zeolites useful in the aromatization reaction have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous Zsm-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Dehydrogenation Catalysts

Paraffin dehydrogenation catalysts also include oxides and sulfides of Groups IVA, VA, VIA, VIIA and VIIIA and mixtures thereof on an inert support such as alumina or silica-alumina. Thus, dehydrogenation may be promoted by sulfides and oxides of titanium, zirconium, vanadium, mobium, tantalum, chromium, molybdenum, tungsten and mixtures thereof. Oxides of chromium alone or in conjunction with other catalytically active species have been shown to be particularly useful in dehydrogenation. Other catalytically active compounds include sulfides and oxides of manganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having dehydrogenation activity. Platinum has been found to be particularly useful for promoting dehydrogenation over zeolite catalysts.

Dehydrogenation Zone Operation

The feedstock is typically heated in a furnace or in a feed/effluent heat exchanger to a temperature approaching that at which coking can occur and is then charged to the dehydrogenation zone at a rate sufficient to maintain the finely divided inert or catalytically active particles in a state of sub-transport fluidization. This facilitates direct heat transfer between the feedstock and the finely divided particles and maintains the fluidized bed at an essentially uniform temperature. The finely divided particles are heated by direct exchange in a separate fluid-bed combustion zone.

As discussed above, the paraffinic feed may crack or dehydrogenate in the dehydrogenation zone. The dominant reaction is determined by reaction temperature and composition of the finely divided solids circulated through the dehydrogenation zone. Dehydrogenation catalysts such as platinum on an inert support and temperatures between about 550° and 705° C. (1020° and 1300° F.) promote paraffin dehydrogenation. Inert solids such as spent fluid catalytic cracking (FCC) catalyst or catalytic solids such as a zeolite without a metal component combined with temperatures between above about 650° C. (1200° F.) favor paraffin cracking to light olefins such as ethylene. By controlling reaction temperature and the composition of the finely divided solids, the overall conversion may be controlled to favor cracking, dehydrogenation or a combination thereof.

The nature and extent of reaction in the dehydrogenation zone is preferably controlled to maintain heat balance in the downstream aromatization zone. For example, ethylene aromatization is more strongly exothermic than heavier olefin aromatization. Consequently, operating the dehydrogenation zone in a cracking mode decreases the extent of reaction required in the dehydrogenation zone to maintain heat balance in the downstream aromatization zone.

The extent of reaction (conversion) in the dehydrogenation zone is controlled by the temperature and space velocity of the paraffinic feed. Lower space velocities provide longer residence time and more complete conversion. In a preferred embodiment of the invention, the dehydrogenation reactor cracks a portion of the paraffinic feed to light olefins, e.g. ethylene, while the remainder of the paraffinic feed is charged directly to the downstream aromatization zone. This configuration typically converts less than 60 wt % of the total paraffinic feed to light olefins rich in ethylene, and minimizes the reactor size for the dehydrogenation zone.

The preferred, or parallel feed, embodiment described above requires a heat source to preheat the portion of the paraffinic feedstream bypassing the dehydrogenation zone. Suitable heat soruces include reactor feed/effluent heat exchangers and fired process furnaces. The paraffinic feed is preferably preheated to a point just below that at which the coke precursors in the feed react to form coke.

In a second and more preferred serial feed embodiment of the invention, the total process unit feedstream is charged to the dehydrogenation zone. The relative degrees of cracking and dehydrogenation are then adjusted by controlling the composition of the finely divided solids within the dehydrogenation zone.

The dehydrogenation zone product selectivity is controlled by adjusting the catalyst composition within the dehydrogenation zone. Specifically, the selectivity toward dehydrogenation rather than cracking may be controlled by the relative amount of dehydrogenation metal present in the dehydrogenation zone. A preferred method is to mix cracking catalyst paricles with dehydrogenation catalyst particles in the dehydrogenation zone. This method maximizes process unit flexibility. As mentioned above, the cracking catalyst may comprise spent catalyst from a fluid catalytic cracking (FCC) process unit, inert solids, or zeolites without a dehydrogenation metal component, to name a few. The dehydrogenation catalyst may comprise a dehydrogenation metal on an inert support or a zeolite or zeolites containing a dehydrogenation metal composited with an inert support, to name two examples. Either cracking or dehydrogenation catalyst may then be added to the dehydrogenation zone catalyst inventory to shift selectivity as desired.

The cooled finely divided particles and the at least partially dehydrogenated preheated feedstock leave the dehydrogenation zone at approximately the same temperature. The operating temperature of the dehydrogenation zone depends on the particulate circulation rate, the feedstock charge rate, the temperature of the finely divided particles at the preheat zone inlet and the feedstock temperature. Particulate circulation ranges broadly between 0.1 and 500 total volumes of finely divided particles per hour, preferably between 2 and 20 total volumes of finely divided particles per hour. The temperature of the finely divided particles entering the dehydrogenation zone is essentially the same as the combustion zone temperature and typically ranges broadly between 600° and 1370° C. (1100° and 2500° F.), preferably about 870° C. (1600° F.). Heat from the finely divided particles is absorbed by the partial dehydrogenation and cracking of the feed.

Fresh feed enters the dehydrogenation zone near the bottom and vaporizes upon contact with the hot finely divided particles. Materials which readily tend to form coke, such as oxygenates or heavy paraffins, react rapidly and are removed from the feedstream in the form of coke deposited on the finely divided particles. To maximize contact between the finely divided particles and the fresh feed, it is preferable to maintain fresh feed flowrate at a rate which will provide sufficient superficial gas velocity to fluidize the finely divided particles in a sub-transport regime. More preferably, the spent catalyst is maintained in a turbulent sub-transport regime to maximize contact between the feedstock and the finely divided particles. Formation of gas bubbles in fluid beds having lower superficial velocities than those required for a turbulent fluidization regime reduces contact between the fluidized particles and the fluidizing gas.

Fuel Gas Stripping

Finely divided particles flowing between the combustion and dehydrogenation zones as well as spent and regenerated catalyst flowing between the aromatization zone and the catalyst regeneration zone are preferably countercurrently stripped with fuel gas.

Hot finely divided particles from the combustion chamber contain entrained combustion products, most notably water. Countercurrently stripping these particles with fuel gas rich in light hydrocarbons including methane, ethane and propane minimizes the steam deactivation of catalyst in the downstream aromatization reactor.

The particles are preferably stripped again as they return from the dehydrogenation zone to the combustion zone. Countercurrently stripping the particles with fuel gas prevents valuable olefinic intermediate product from being burned in the combustion zone.

Description of the Preferred Embodiment

Referring now to the Figure, a preferred embodiment of the process of the present invention is described beginning at the inlet of the combustion vessel and proceeding through the dehydrogenation and aromatization reactors.

Compressed oxygen-containing, combustion gas, typically air, flows through line 10 and is joined by finely divided particles from line 11. Line 11 is equipped with control valve 12. The finely divided particles are fluidized in the combustion gas stream in a transport flow regime and continue upward through line 10, entering a dense fluid bed of finely divided particles 18 located in a lower section of combustion vessel 14. As noted above, the finely divided particles circulating through combustion vessel 14 and dehydrogenation vessel 44 may comprise inert particles, spent fluid cracking catalyst (FCC catalyst), a zeolite composited with an inert binder, dehydrogenation metal on an inert support or a combination of two or more of these materials. As the fluidized mixture of finely divided particles and combustion gas flows into combustion vessel 14, the mixture passes through distributor grid 16 to evenly distribute the combustion gas and finely divided particles through the dense bed.

Fuel is charged to a lower section of combustion vessel 14 through line 20. Charge rates of fuel flowing through line 20 and combustion gas flowing through line 10 are preferably maintained at a rate sufficient to maintain the fluid bed temperature above about 870° C. (1600° F.) while fluidizing the finely divided particles in a sub-transport regime. The fuel is preferably hydrogen deficient to minimize introduction of water into the system, Cyclones 28 positioned near the top of combustion vessel 14 separate finely divided inert particles from flue gas generated in the combustion vessel. Finely divided particles are returned to the dense bed 18 via diplegs 26, while flue gas flows first to a plenum chamber 29 and then is exhausted from the combustion vessel through line 30. The hot flue gas is then cooled in a heat recovery unit, for example, a steam generation unit, to a temperature below about 190° C. (375° F.) and is subsequently exhausted to atmosphere. Sintered metal filters may optionally be installed in line 30 to further remove fines from the flue gas stream.

Hot finely divided solids flow to dehydrogenator 44 through line 22 which is equipped with flow control valve 24. Line 15 introduces fuel gas which is preferably rich in ethane and propane into line 22 to countercurrently strip combustion products from the hot finely divided solids. The fuel gas is then dehydrogenated or cracked in the dehydrogenation reactor and subsequently upgraded to valuable aromatic product.

An aliphatic feed, typically rich in paraffins, enters the bottom of dehydrogenator 44 through line 40 and flows upward through distributor grid 42 which is positioned in a lower section of dehydrogenator 44. At least a portion of the paraffins in the aliphatic feedstream are dehydrogenated or cracked to olefins in dehydrogenator 44. The extent and selectivity of the dehydrogenation/cracking reaction is controlled to heat balance the downstream aromatization reactor. The finely divided solids are cooled in the dehydrogenator as paraffins crack and dehydrogenate to form an intermediate product. Cooled finely divided particles are withdrawn from dehydrogenator 44 through line 11 and returned to combustion vessel 14 for reheating as described above. Line 13 countercurrently charges fuel gas to line 11 to strip valuable cracked and/or dehydrogenated product from the finely divided particles.

Cyclone 46 is positioned in dehydrogenator 44 near the top and separates finely divided particles from the intermediate product which flows out of dehydrogenator 44 through line 48.

The intermediate product withdrawn from dehydrogenator 44 is richer in olefins than the aliphatic feedstream entering dehydrogenator 44 and has been preheated for dehydrocyclization to a temperature of between about 540° and 820° C. (1000° and 1500° F.). The conversion of paraffins to olefins in dehydrogenator 44 is highly endothermic. Depending on the extent of conversion in dehydrogenator 44, the reaction in downstream aromatization reactor 50 may range from endothermic to essentially heat balanced to exothermic. Preferably, conversion in dehydrogenator 44 is controlled to heat balance the aromatization reactor.

The intermediate product stream flowing through line 48 enters a dense fluidized bed of aromatization catalyst 54 maintained in a lower section of aromatization reactor 50. The intermediate product stream flows through a distributor 52 positioned near the bottom of aromatization reactor 50 to ensure uniform contact between the intermediate product stream and the aromatization catalyst.

Aromatization reactor 50 is sized to maintain the aromatization catalyst in a state of sub-transport fluidization. Aromatized product is separated from the finely divided aromatization catalyst in cyclones 58 which are positioned near the top of aromatization reactor 50. Diplegs 56 return the finely divided aromatization catalyst to the dense bed 54, while the aromatized product flows to plenum chamber 59 and proceeds to a product recovery section via line 60.

During the course of the aromatization reaction, coke masks the active sites of the aromatization catalyst, thereby causing an at least partial reduction in catalytic activity. A stream of partially deactivated aromatization catalyst is withdrawn from a lower portion of aromatization reactor 50 through line 62 which is equipped with control valve 64. Line 63 charges fuel gas which is preferably rich in ethane and propane to line 62 to countercurrently strip valuable aromatization reactor product from the spent catalyst. The stripped aromatization catalyst the flows to line 66 where it is fluidized in a transport regime in a stream of oxygen-containing gas, typically air. The fluidized mixture enters a dense bed of aromatization catalyst 70 in a lower section of continuous regenerator 68. Distributor grid 71 is positioned near the bottom of continuous regenerator 68 to provide even distribution of regeneration gas and catalyst across the vessel. Regenerated catalyst is withdrawn from continuous regenerator 68 through line 72 which is equipped with flow control valve 74 and is returned to aromatization reactor 50. Line 73 charges fuel gas rich in ethane and propane to line 72 to strip combustion products from the regenerated catalyst before it enters aromatization reactor 50.

Cyclones 78 separate regenerator flue gas from regenerated aromatization catalyst. Diplegs 76 return the regenerated aromatization catalyst to dense bed 70, while the regenerator flue gas flows first to regenerator plenum chamber 79 and then exits the regenerator through line 80.

Changes and modifications in the specifically described embodiments can be carried out without departing from the scope of the invention which is intended to be limited only by the scope of the appended claims.

What is claimed is:

1. A process for the aromatization of an aliphatic feedstream comprising the steps of:
    (a) fluidizing finely divided solid particles in a combustion zone;
    (b) charging oxygen-containing combustion gas and fuel to said combustion zone under combustion conditions;
    (c) withdrawing a stream of finely divided particles from said combustion zone;
    (d) flowing said withdrawn stream of finely divided particles of step (c) above to a cracking/dehydrogenation zone;
    (e) fluidizing said finely divided particles of step (d) above in an aliphatic feedstream under conditions within said cracking/dehydrogenation zone controlled to at least partially crack and at least partially dehydrogenate said aliphatic feedstream to form an intermediate product stream containing a quantity of $C_4$-olefins such that the exothermic catalytic conversion of said $C_4$-olefins is sufficient to supply a portion of the endothermic heat of reaction for the endothermic catalytic conversion of paraffins contained in said intermediate feedstream to aromatics;
    (f) contacting said intermediate product stream with an aromatization catalyst under aromatization conditions sufficient to evolve an aromatics-rich products stream.

2. The process of claim 1 wherein step (f) further comprises contacting said intermediate product stream with a fluid bed of aromatization catalyst.

3. The process of claim 1 wherein step (f) further comprises contacting said intermediate product stream with a moving bed of aromatization catalyst.

4. The process of claim 1 wherein said finely divided solid particles comprise at least partially deactivated cracking catalyst.

5. The process of claim 1 wherein said finely divided solid particles are catalytically inert.

6. The process of claim 1 wherein said solid particles comprise a dehydrogenation catalyst and said conversion conditions recited in step (e) above comprise conditions sufficient to partially dehydrogenate and partially crack said aliphatic feedstream.

7. The process of claim 6 wherein said finely divided solid particles comprise a metal on an inert support.

8. The process of claim 6 wherein said finely divided particles comprise a metal-containing zeolite composited with a binder.

9. The process of claim 8 wherein said metal is platinum.

10. The process of claim 1 wherein said conversion conditions of step (e) include temperatures between 550° and 705° C. (1020° and 1300° F.).

11. The process of claim 1 wherein said conversion conditions of step (e) include temperatures between 550° and 705° C. (1020° and 1300° F.), pressures between 170 and 2170 kPa (10 and 300 psig) and weight hourly space velocity between 0.3 and 300 $hr^{-1}$.

12. The process of claim 1 wherein said aromatization catalyst comprises a zeolite.

13. The process of claim 1 wherein said aromatization catalyst comprises a zeolite having a Constraint Index between about 1 and about 12.

14. The process of claim 13 wherein said zeolite has the structure of at least one of the group consisting of ZSM-5, ZSM-11, ZSM-22, ZSM-23, ZSM-35 and ZSM-48.

15. The process of claim 14 wherein said zeolite contains gallium.

16. The process of claim 1 wherein said aromatization conversion conditions include temperatures between 500° and 820° C. (930° and 1500° F.), pressures between 170 and 2170 kPa (10 and 300 psig) and weight hourly space velocity between 0.3 and 300 $hr^{-1}$.

17. The process of claim 1 further comprising stripping combustion products from said stream of finely divided particles of step (c) above by countercurrently contacting said stream of finely divided particles with fuel gas containing $C_3$-aliphatic hydrocarbons.

18. The process of claim 1 further comprising withdrawing a stream of finely divided particles from said cracking/dehydrogenation zone and stripping said stream of finely divided particles by countercurrently contacting said stream of finely divided particles with fuel gas containing $C_3$-aliphatic hydrocarbons.

19. The process of claim 1 further comprising withdrawing at least partially deactivated aromatization catalyst from said aromatization zone and stripping said catalyst by countercurrently contacting said catalyst with fuel gas containing $C_3$-aliphatic hydrocarbons.

20. The process of claim 1 further comprising withdrawing at least partially deactivated aromatization catalyst from said aromatization zone, oxidatively regenerating said catalyst to form regenerated catalyst and returning said regenerated catalyst to said aromatization zone.

21. The process of claim 20 further comprising stripping said deactivated catalyst by countercurrently contacting said deactivated catalyst with fuel gas containing $C_3$-aliphatic hydrocarbons.

22. The process of claim 20 further comprising stripping said regenerated catalyst by countercurrently contacting said regenerated catalyst with fuel gas containing $C_3$-hydrocarbons.

23. A process for the heat balanced aromatization of an aliphatic feedstream comprising the steps of:
   (a) fluidizing finely divided particles in a combustion zone;
   (b) charging oxygen-containing combustion gas and fuel to said combustion zone under combustion conditions;
   (c) withdrawing a stream of finely divided particles from said combustion zone;
   (d) flowing said withdrawn stream of finely divided particles of step (c) to a cracking/dehydrogenation zone;
   (e) fluidizing said finely divided particles of step (d) in an aliphatic feedstream in said cracking/dehydrogenation zone;
   (f) controlling the composittion of said finely divided particles as well as conversion conditions including temperature and space velocity in said cracking-/dehydrogenation zone to at least partially crack and at least partially dehydrogenate said aliphatic feedstream to form an intermediate product stream having a sufficient fraction of $C_4$- olefins to provide substantially heat balanced aromatization of said intermediate product stream upon contact with a zeolite aromatization catalyst under aromatization conversion conditions;
   (g) contacting said intermediate product stream with a zeolite aromatization catalyst under aromatization conditions to evolve an aromatics-rich product stream.

24. A process for the heat balanced aromatization of aliphatic hydrocarbons comprising the steps of:
   (a) fluidizing finely divided particles in a combustion zone;
   (b) charging oxygen-containing combustion gas and fuel to said combustion zone under combustion conditions;
   (c) withdrawing a stream of finely divided particles from said combustion zone;
   (d) flowing said withdrawn stream of finely divided particles of step (c) above to a cracking/dehydrogenation zone;
   (e) fluidizing said finely divided particles of step (d) above in a first aliphatic feedstream in said cracking/dehydrogenation zone under conversion conditions to form an intermediate product stream;
   (f) contacting said intermediate product stream together with a second aliphatic feedstream with a zeolite aromatization catalyst in an aromatization zone, under aromatization conditions to evolve an aromatics-rich product stream;
   (g) controlling the composition of said finely divided particles as well as conversion conditions including temperature and space velocity in said cracking-/dehydrogenation zone to at least partially crack and at least partially dehydrogenate said first aliphatic feedstream to form an intermediate product stream having a sufficient fraction of $C_4$-olefins to produce substantially heat balanced aromatization of said intermediate product stream and said second aliphatic feedstream in said aromatization zone.

* * * * *